United States Patent

Sasaki et al.

Patent Number: 5,164,507
Date of Patent: Nov. 17, 1992

[54] ANTIBIOTIC PYRIDINE COMPOUND

[75] Inventors: Toru Sasaki; Akira Shimizu; Junko Yoshida; Hiroomi Watabe; Masao Koyama, all of Kanagawa, Japan

[73] Assignee: Meiji Seika Kaisha Ltd., Tokyo, Japan

[21] Appl. No.: 703,653

[22] Filed: May 21, 1991

[30] Foreign Application Priority Data

May 21, 1990 [JP] Japan ................... 2-129049

[51] Int. Cl.$^5$ ............................. C07D 211/68
[52] U.S. Cl. ............................. 546/310
[58] Field of Search ........................ 546/310

[56] References Cited

FOREIGN PATENT DOCUMENTS 0207674 1/1987 European Pat. Off. ............ 546/310
0244713 11/1987 European Pat. Off. ............ 546/310

OTHER PUBLICATIONS

The Chemistry of Extractives for Hardwoods, Part III pp. 3590-3597.
Chemical & Pharmaceutical Bulletin, vol. 35, No. 8, Aug. 1987, Japan, pp. 3482-3486; 'Genjiro Kusano et al.: A New Amino Acid, (2s,3r)-(−)-3-Hydroxybaikiain from Russula subnigricans Hongo' p. 3483; FIG. 2.

*Primary Examiner*—Warren C. Ivy
*Assistant Examiner*—Zinna Northington Davis
*Attorney, Agent, or Firm*—Sughrue, Mion, Zinn, Macpeak & Seas

[57] ABSTRACT

A substance represented by formula:

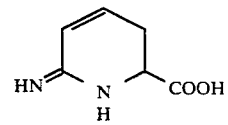

and a salt thereof, which has antifungal activity and a process for producing the same utilizing a microorganism capable of producing the substance and belonging to the genus Streptomyces.

2 Claims, 1 Drawing Sheet

ANTIBIOTIC PYRIDINE COMPOUND

FIELD OF THE INVENTION

This invention relates to a novel antibiotic which is expected to be useful as a treating agent of mycoses and to a process for preparing the same.

BACKGROUND OF THE INVENTION

A number of antibiotics produced by microorganisms have hitherto been developed, but a compound consistent with the antibiotic substance of the present invention (hereinafter referred to as "substance SF 2698") in physicochemical properties is not among them.

While various antibiotics are known and have been practically used in the fields of pharmaceuticals, veterinary drugs, and agricultural chemicals, there has been a constant demand for a novel antibiotic having higher safety and more effectiveness particularly in the field of antifungals.

SUMMARY OF THE INVENTION

An object of the present invention is provide a novel antibiotic with antifungal activity.

Another object of the present invention is to provide a process for preparing such an antibiotic.

To meet the above-described demand, the inventors have searched for a substance with antifungal activity and, as a result, have found a culture of a certain strain belonging to the genus Streptomyces to have produced a substance which exhibits antifungal activity in a synthetic medium. They have isolated the effective substance and determined its physicochemical properties.

The above-described objects of the present invention are attained by a novel antibiotic substance SF 2698 represented by formula:

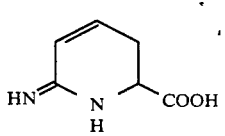

and salts thereof and a process for preparing substance SF 2698, which comprises cultivating a microorganism belonging to the genus Streptomyces and capable of producing substance SF 2698 in a medium to accumulate substance SF 2698 therein and recovering the accumulated substance SF 2698.

DETAILED DESCRIPTION OF THE INVENTION

Figure 1:
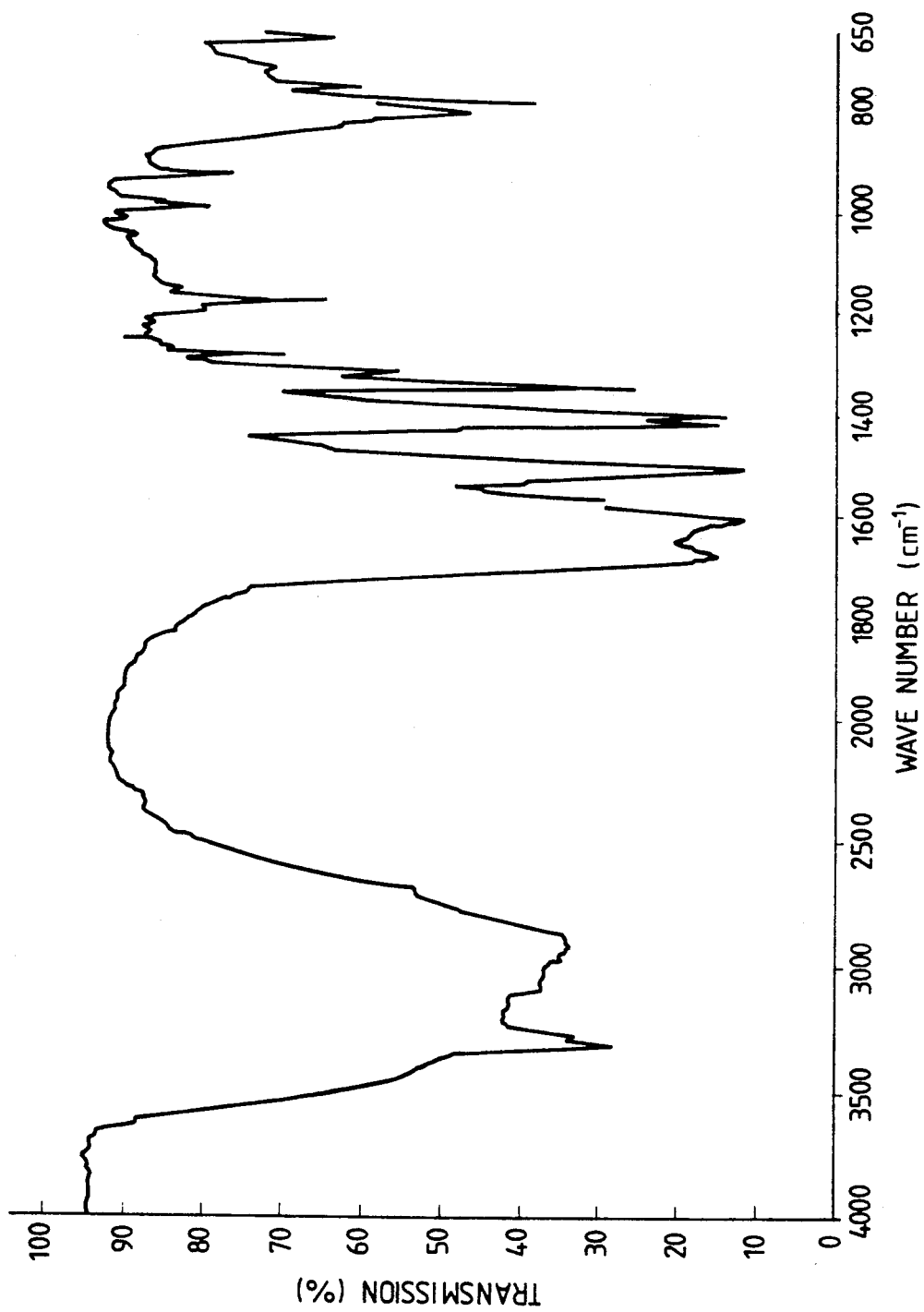
FIG. 1 is an infrared absorption spectrum (KBr tablet) of a hydrochloride of substance SF 2698.

A hydrochloride of substance SF 2698 has the following physicochemical properties:

1) Color and shape: colorless crystal
2) Melting point: vague; decomposition at 250° C. or higher
3) Molecular formula: $C_6H_8N_2O_2$
4) Mass spectrum (HR-MS): Calcd.: m/z 140.0585 ($C_6H_8N_2O_2$). Found : m/z 140.0587 ($M^+$).

Specific rotation: $[\alpha]_D^{25}$ $-50°$ (c=1.0, $H_2O$)

Ultraviolet and visible absorption spectra: $\lambda_{max}$ nm ($\epsilon$)[MeOH]: 218 (9000), 255 (shoulder)

7) Infrared absorption spectrum: shown in FIG. 1
8) $^1H$ NMR spectrum (400 MHZ, $D_2O$): δ (ppm): 7.02 (1H, dt), 6.23 (1H, dt), 4.18 (1H, t), 2.92 (1H, m), 2.78 (1H, m)
9) $^{13}C$ NMR spectrum (100 MHz, $D_2O$): δ (ppm): 177.8 s, 159.1 s, 146.9 d, 117.3 d, 53.4 d, 27.8 t
10) Solubility: soluble in water or methanol; insoluble in organic solvents, e.g., ethyl acetate
11) Color reaction: positive with a Greig-Leaback (GL) reagent and a pentacyanoaquoferroate reagent, and develops a yellow color with a ninhydrin reagent Thin layer chromatography (TLC): Rf=0.29; silica gel glass plate (5715, manufactured by Merck Co.); butanol-methanol-water (2:1:1 by volume) as a developing solvent From the above-described physicochemical properties combined with results of instrumental analyses, the substance SF 2698 is deemed to be a novel substance which has never been reported and is represented by formula:

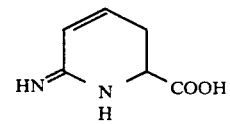

Substance SF 2698 may have the following alternative structure depending on conditions.

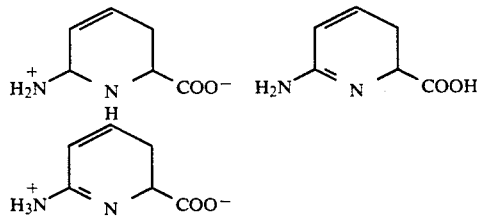

Substance SF 2689 is an amphoteric substance and can be converted to inorganic or organic acid salts, e.g., a hydrochloride, a sulfate, and a trifluoroacetate, or salts with inorganic or organic bases, e.g., a sodium salt, a potassium salt, and an ethanolamine salt.

Substance SF 2698-producing microorganisms which can be used in the present invention include a strain SF 2698 isolated from the soil of Shizuoka, Japan.

Strain SF 2698 has the following microbiological properties.

I. Morphological characteristics

Vegetative hyphae extend long and branch well, and are not cut under usual conditions. Aerial hyphae abundantly grow on a starch-agar medium, a glucose-asparagine-agar medium, etc. with satisfactory sporulation. Branching of aerial hyphae is relatively small with no whirl branching. Spore chains on the top of aerial hyphae are linear. Under electron microscopic observation, spores have an elliptic to cylindrical shape having a size of from 0.6–1.0×0.9–1.4 μm and with a smooth surface. Usually about 30 to 50 spores are linked. No sporangium, no motile spore or no sclerotium is observed.

II. Growth condition on various media

Growth conditions of strain SF 2698 on various media are shown in Table below. Color standards in parentheses are in accordance with *Color Harmony Manual* of Container Corporation of America. Observations were made after cultivation at 28° C. for 14 to 21 days.

| Medium | Growth (Color of Reverse of Colony) | Aerial Hypha | Soluble Pigment |
|---|---|---|---|
| sucrose-nitrate-agar | medium; pearl (2ba) | medium, pearl (2ba) | none |
| glucose-asparagine-agar | satisfactory; pale yellow (2fb) | medium to satisfactory, pastel yellow (1fb) | none |
| glycerine-asparagine-agar | medium; pale yellow (1ba) | poor; pearl (2ba) | none |
| malic acid-calcium-agar | medium; pearl (2ba) | medium; pearl (2ba) | none |
| starch-agar | satisfactory; pale yellow (2fb) | satisfactory; pastel yellow (1fb) | none |
| oat meal-agar | satisfactory; pale yellow (2fb) | medium; ivory-white (2ca) | ivory-white (2ca) |
| yeast extract-malt extract-agar | satisfactory; | satisfactory; mustard (2le) | none faint yellow (1ca) |
| tyrosine-agar | medium; yellowish brown (2ie) | poor; pearl (2ba) | none |
| nutrient agar | medium; grayish yellow (2gc) | none | none |
| Bennett agar | satisfactory; mustard (2le) | satisfactory; faint yellow (1ca) | none |

III. Physiological properties (1) Range of growth temperature condition: from 15° to 33° C., and particularly from 25° to 30° c., on a yeast extract-starch-agar medium.

(2) Gelatin liquefaction: negative (3) Starch hydrolysis: negative (4) Reduction of nitrate: positive (5) Peptonization of skim milk: negative Coagulation of skim milk: negative (6) Salt resistance: capable of growing in a 5% NaCl-containing medium but substantially incapable of growing in a 7% or higher NaCl-containing medium (7) Melanin-like pigment production: positive (on peptone-yeast-iron agar medium)

IV. Utilization of carbon sources (on ISP-9 medium)

(1) Utilizable: D-glucose, D-fructose, glycerol, D-mannitol, raffinose (2) Non-utilizable: L-arabinose, L-rhamnose, sucrose (3) Doubtfully utilizable: D-xylose, myo-inositol

V. Analysis of microbial cells

Analysis by Becker's method (*Appl. Microbiol.*, 13:236 (1965) revealed that the diaminopimelic acid in the hydrolysate of the whole microbial cells was LL type.

From these taxonomical properties, strain SF 2698 is recognized to be a strain belonging to the genus Streptomyces of actinomyces, with the aerial hypha in the "yellow" color series, the tip of the aerial hypha being linear, a smooth spore surface, and a reverse color being from pale yellow to yellowish brown, and dose not produce an appreciable soluble pigment. The inventors designated the strain Streptomyces sp. SF 2698. The strain has been deposited to Fermentation Research Institute, Agency of Industrial Science & Technology (1-3, Higashi 1-chome, Tsukuba-shi, Ibaraki 305 JAPAN) under a receipt number of FERM BP-3336 in accordance with the Budapest Treaty.

Properties of strain SF 2698 are liable to undergo variation as usually observed with other actinomyces. All the mutants (either spontaneous or induced), zygotes or recombinants of, or originated from, strain SF 2698 can be used in the present invention if they can produce substance SF 2698.

The above-described strain is cultivated in a medium containing nutrients generally utilizable by microorganisms. Any of known nutrient sources conventionally utilized for cultivation of actinomyces can be used. Examples of usable carbon sources are glucose, glucose or maltose syrup, dextrin, starch, molasses, and animal and vegetable oils. Examples of usable nitrogen sources are soybean meal, wheat germs, corn steep liquor, cotton seed meal, meat extract, peptone, yeast extract, ammonium sulfate, sodium nitrate, and urea. If necessary, inorganic acid salts capable of producing a sodium, potassium, calcium, magnesium, cobalt, chloride, phosphate or sulfate ion or other ions are added to the medium. Examples of the inorganic acid salts include sodium sulfate and calcium carbonate. Organic or inorganic substances which assist growth of the strain to accelerate production of antibiotic SF 2698 are appropriately added to the medium. Specific examples thereof are Vitamin A, $B_1$, $B_2$ and $B_{12}$.

Cultivation is suitably carried out under aerobic conditions, and particularly by submerged culture, at pH 7.5 and at a temperature of from 25° to 30° C., mostly around 28° C. Accumulation of substance SF 2698 reaches the maximum usually at 2 to 7 day culture either in shake culture or static culture, though depending on the medium and culture conditions. When the amount of accumulated substance SF 2698 reaches the maximum, cultivation is stopped, and the desired substance is isolated and purificated from the culture supernatant.

Means for isolation and purification of substance SF 2698 from the culture are selected from those generally employed making use of the properties of the substance, such as ion exchange resin methods, adsorption or partition column chromatography, gel filtration, dialysis, sedimentation, and the like either individually or in an appropriate combination thereof. For example, substance SF 2698 produced and accumulated in the culture is adsorbed onto strongly acidic ion exchange resins, e.g., Diaion PK-208 (produced by Mitsubishi Kasei Corporation). It is effectively purified by chromatography using an adsorbent, e.g., activated carbon. For further purification of substance SF 2698, chromatography using an adsorbent, e.g., silica gel (Wako Gel C-200, produced by Wako Pure Chemical Industries, Ltd.), alumina, etc., or Sephadex G-10 (produced by Pharmacia Co.). If desired, the above chromatographic methods may be used in combination in an appropriate order. The novel substance SF 2698 according to the present invention exhibits antifungal activity as demonstrated by Test Example hereinafter described and is applicable to therapy of mycoses in humans and animals with expectation of usefulness as an antifungal. For therapeutic use, substance SF 2698 can be formulated into a pharmaceutical composition of various dosage forms according to known preparation techniques. Substance SF 2698 may also be utilized as an intermediate for synthesizing pharmaceuticals.

TEST EXAMPLE

Minimum growth inhibitory concentrations (MIC) of a hydrochloride of substance SF 2698 on various test microorganisms are shown in Table 1 below.

TABLE 1

| Test Microorganism | MIC (μg/ml) |
|---|---|
| Candida glabrata IFO-0005 | 0.2 |
| Candida glabrata IFO-0622 | 0.78 |
| Candida utilis M9007 | 12.5 |
| Candida albicans M9001 | >100 |
| Cryptococcus neoformans M9010 | >100 |

As is apparent from Table 1, a hydrochloride of substance SF 2698 exhibits antimicrobial activity against certain kinds of eumycetes.

Further, toxicity of a hydrochloride of substance SF2698 was examined by administering to mice the test compound by intravenous injection. As a result, there was no case of death at a dose of 100 mg/kg.

The present invention is now illustrated in greater detail with reference to Example. Now that properties of substance SF 2698 have been elucidated, various approaches can be taken for the preparation of substance SF 2698 according to its properties. Hence, the present invention is not deemed to be limited to the Example described. The present invention also include methods of production, concentration, extraction, purification of substance SF 2698 according to its properties using known methods as well as modifications of the methods described in Example.

EXAMPLE

A medium comprising 1.0% of starch, 1.0% of glucose, 0.5% of polypeptone, 0.3% of yeast extract, 0.2% of soybean meal, and 0.2% of meat extract (pH=7.0 before sterilization) was used as a seed medium.

A medium comprising 5.0% of glucose (separately sterilized), 2.5% of soybean meal, 0.2% of meat extract, 0.2% of polypeptone, 0.2% of yeast extract, 0.2% of sodium sulfate (anhydrous), and 0.5% of calcium carbonate (pH=6.0 before sterilization) was used as a production medium.

A 100 ml-volume Erlenmeyer flask containing 20 ml of the seed medium was sterilized at 121° C. for 20 minutes, and 2 to 3 platinum loopfuls of a slant agar culture of Streptomyces sp. SF 2698 (FERM BP-3336) were inoculated thereto and cultivated at 28° C. for 24 hours with shaking to prepare a first subculture.

A 500 ml-volume Erlenmeyer flask containing 80 ml of the seed medium was sterilized at 121° C. for 30 minutes, and 4 ml of the first subculture was inoculated thereto and cultivated at 28° C. for 24 hours with shaking to prepare a second subculture.

A 2 l-volume Erlenmeyer flask containing 700 ml of the seed medium was sterilized at 121° C. for 30 minutes, and 35 ml of the second subculture was inoculated thereto and cultivated at 28° C. for 24 hours to prepare a third subculture.

700 ml of the third subculture was inoculated to a 50 l-volume jar fermenter containing 35 l of the production medium was sterilized at 121° C. for 30 minutes and cultivated at 28° C. for 5 days with aeration (17.5 l/min) and stirring (250 rpm in the initial stage; 400 rpm from 24 hours on).

After completion of the cultivation, diatomaceous earth was added to the culture as a filter aid, and the culture was filtered. The filtrate of the culture (60 l) was passed through a column of activated carbon for chromatography (6 l), and the column was washed with water (40 l). The washing was concentrated under reduced pressure, and the concentrate (4 l) was passed through a column of Diaion PK-208 (H+ type, 800 ml; produced by Mitsubishi Kasei Corporation). After washing the column with water, elution was carried out using 0.1N aqueous ammonia (13 l). The eluent containing the active component was determined by bioassay using Candida glabrata as the indicator microorganism and neutralized with 0.5N hydrochloric acid and passed through a column of activated carbon for chromatography (1 l). After washing the column with water, the active component was eluted with 30% aqueous methanol (2 l). The eluent was concentrated under reduced pressure, and the concentrate was subjected to chromatography using a column of Sephadex G-10 (1.8 l; produced by Pharmacia Co.) and water as a developing solvent. The active fraction was concentrated under reduced pressure at 40° C. or less to obtain 103 mg of a hydrochloride of substance SF 2698 as a colorless crystal.

Substance SF 2698 per se can be obtained from the above active fraction as follows. The fraction is adjusted to pH 5 and was desalted by activated carbon chromatography. The resulting eluate is concentrated to dryness under reduced pressure to give substance SF 2698.

While the invention has been described in detail and with reference to specific examples thereof, it will be apparent to one skilled in the art that various changes and modifications can be made therein without departing from the spirit and scope thereof.

What is claimed is:

1. A compound represented by formula:

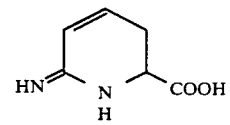

or a salt thereof.

2. A compound whose hydrochloride has the following physicochemical properties:
   1) Color and shape: colorless crystal
   2) Melting point: vague; decomposition at 250° C. or higher
   3) Molecular formula: $C_6H_8N_2O_2\cdot\frac{1}{2}HCl$
   4) Mass spectrum (HR-MS): Calcd.: m/z 140.0585 ($C_6H_8N_2O_2$). Found: m/z 140.0587 (M+).
   5) Ultraviolet and visible absorption spectra: $\lambda_{max}$ nm (ε)[MeOH]: 218 (9000), 255 (shoulder)
   6) $^{13}C$ NMR spectrum (100 MHz, $D_2O$): δ (ppm): 177.8 s, 159.1 s, 146.9 d, 117.3 d, 53.4 d, 27.8 t.

* * * * *